(12) United States Patent
Negishi et al.

(10) Patent No.: US 7,442,531 B2
(45) Date of Patent: Oct. 28, 2008

(54) METHOD FOR PRODUCING SYMMETRIC TRIGLYCERIDES

(75) Inventors: Satoshi Negishi, Yokosuka (JP); Yuri Arai, Yokosuka (JP); Shin Arimoto, Yokosuka (JP); Hidetaka Uehara, Yokosuka (JP)

(73) Assignee: The Nisshin OilliO Group, Ltd., Chuo-Ku, Tokyo (JP)

( * ) Notice: Subject to any disclaimer, the term of this patent is extended or adjusted under 35 U.S.C. 154(b) by 380 days.

(21) Appl. No.: 11/326,436

(22) Filed: Jan. 6, 2006

(65) Prior Publication Data

US 2006/0115882 A1    Jun. 1, 2006

Related U.S. Application Data

(63) Continuation of application No. PCT/JP2004/009307, filed on Jun. 24, 2004.

(30) Foreign Application Priority Data

Jul. 9, 2003     (JP)     ............................. 2003-194322

(51) Int. Cl.
    *C12P 7/64*     (2006.01)
(52) U.S. Cl. ..................................... 435/134
(58) Field of Classification Search .................. 435/134
    See application file for complete search history.

(56) References Cited

U.S. PATENT DOCUMENTS

| 4,268,527 | A |   | 5/1981  | Matsuo et al. |
|-----------|---|---|---------|---------------|
| 4,364,868 | A | * | 12/1982 | Hargreaves ................ 554/169 |
| 4,956,287 | A | * | 9/1990  | Suzuki et al. .............. 435/134 |
| 5,149,642 | A | * | 9/1992  | Mazur et al. ............... 435/135 |
| 5,286,633 | A | * | 2/1994  | Moore ........................ 435/134 |
| 5,304,427 | A | * | 4/1994  | Benz et al. ................. 428/567 |
| 5,508,048 | A | * | 4/1996  | Padley ......................... 426/33 |
| 6,369,252 | B1 |  | 4/2002  | Akoh |
| 6,737,100 | B1 | * | 5/2004  | Matsui et al. .............. 426/631 |

FOREIGN PATENT DOCUMENTS

| EP | 185524 | * | 6/1986 |
| EP | 273352 | * | 7/1987 |
| JP | 57-27159 | B2 | 6/1982 |
| JP | 63240790 | * | 11/1987 |
| JP | 7-83718 | B2 | 9/1995 |
| JP | 7-89944 | B2 | 10/1995 |
| JP | 11-243982 | A |  | 9/1999 |
| JP | 2000-270885 | A | 10/2000 |

OTHER PUBLICATIONS

Xu et al., "Pilot Batch Production of Specific-Structured Lipids by Lipase-Catalyzed Interesterification: Preliminary Study of Incorporation and Acyl Migration," *J. Am. Oil Chem. Soc.*, 1998, pp. 301-308, vol. 75, No. 2.

Irimescu et al., "Enzymatic Synthesis of 1,3-Dicapryloyl-2-eicosapentaenoylglycerol," *J. Am. Oil Chem. Soc.*, 2000, pp. 501-506, vol. 77, No. 5.

Iwasaki et al., "Enzymatic synthesis of structured lipids," *J. of Molecular Catalysis B: Enzymatic*, 2000, pp. 129-140, vol. 10, Elsevier Science B.V.

Iwasaki et al., "Enzymatic Syntheses of Structured Lipids," *J. Oleo Science*, 2001, pp. 4-13, vol. 1, No. 8 (English abstract).

Satoshi Negishi et al.; "Synthesis of 1,3-Dicapryloyl-2-docosahexaenoylglycerol by a Combination of Nonselective and sn-1,3-Selective Lipase Reactions"; Journal of the American Oil Chemists' Society; 2003; pp. 971-974; vol. 80-No.10; AOCS Press, Champaign, IL, USA.

Roxana Irimescu et al.; "Comparison of Acyl Donors for Lipase-Catalyzed Production of 1,3-Dicapryloyl-2-eicosapentaenoylglycerol"; Journal of the American Oil Chemists' Society; 2001; pp. 65-70; vol. 78-No.1; AOCS Press. Champaign, IL, USA.

* cited by examiner

*Primary Examiner*—Herbert J. Lilling
(74) *Attorney, Agent, or Firm*—Buchanan Ingersoll & Rooney PC

(57) ABSTRACT

A method for producing symmetric triglycerides, which comprises the steps of reacting a medium chain fatty acid triglyceride with a long chain fatty acid triglyceride in the presence of an enzyme or a chemical catalyst to conduct random transesterification reaction and thereby to obtain a reaction product containing a triglyceride composed of a medium chain fatty acid and a long chain fatty acid as the constituting fatty acids in the step of the first reaction; transesterifying the reaction product with an alcohol monoester of the medium chain fatty acid in the presence of an sn-1,3-position specific enzyme in the step of the second reaction and then taking the alcohol monoester of the medium chain fatty acid and the alcohol monoester of the long chain fatty acid from the reaction product obtained in the step of the second reaction to obtain the symmetric triglyceride composed of the medium chain fatty acids at the sn-1, 3 positions and the long chain fatty acid at the sn-2 position. According to this method, highly pure symmetric triglycerides comprising a medium-chain fatty acid at sn-1 and 3 positions and a long chain fatty acid at sn-2 position can be industrially efficiently produced.

22 Claims, 2 Drawing Sheets

METHOD FOR PRODUCING SYMMETRIC TRIGLYCERIDES

BACKGROUND OF THE INVENTION

The present invention relates to a method for producing symmetric triglycerides comprising a medium-chain fatty acid at sn (stereo-specific numbering)-1 and 3 positions and a long chain fatty acid at sn-2 position. In particular, the present invention relates to a method for industrially efficiently producing highly pure symmetric triglycerides comprising a medium-chain fatty acid at sn-1 and 3 positions and a long chain fatty acid at sn-2 position.

Various reports were made on methods for producing symmetric triglycerides comprising a fatty acid A at sn-1 and 3 positions and a long chain fatty acid B at sn-2 position in the field of basic research. Methods for producing symmetric triglycerides comprising a long-chain fatty acid as the constituent fatty acid include, for example, a method wherein a triglyceride bonded with oleic acid at the sn-2 position is reacted with sn-1,3 position-specific lipase to produce a triglyceride bonded with oleic acid at the sn-2 position. This method is for producing a cacao butter substitute (see, for example, Japanese Patent Publication for Opposition Purpose (hereinafter referred to as "J. P. KOKOKU") Nos. Hei 07-83718 and Sho 57-27159, and Japanese Patent Un-Examined Publication (J P Kokai) No. Hei 11-243982). Methods for producing symmetric triglycerides having a polyvalent unsaturated fatty acid at the sn-2 position include, for example, a method wherein an oil or fat containing polyvalent unsaturated fatty acids in a large amount is reacted with a saturated fatty acid and/or an alcohol ester of a saturated fatty acid in the presence of an sn-1,3-position specific lipase (refer to, for example, J. P. KOKOKU No. Hei 07-89944). However, highly pure symmetric triglycerides comprising a medium-chain fatty acid at sn-1 and 3 positions and a long chain fatty acid at sn-2 position cannot be obtained by those methods.

For producing symmetric triglycerides (hereinafter referred to as MLM-type triglycerides) (M: medium chain fatty acid, L: long chain fatty acid) comprising a medium-chain fatty acid at sn-1 and 3 positions and a long chain fatty acid at sn-2 position, for example, the following methods are described in Yugo Iwasaki and Tsuneo Yamane, "Oleoscience" 2001, Vol. 1, No. 8, 825-833:

(1) A method wherein a medium chain fatty acid triglyceride is transesterified with a long chain fatty acid triglyceride in the presence of an sn-1,3-position specific lipase.

(2) A method wherein a long chain fatty acid triglyceride is subjected to an acidlysis reaction with an excess amount of a medium chain fatty acid or a method wherein a long chain fatty acid triglyceride is transesterified with an excess amount of an ethyl ester of a medium chain fatty acid.

MLM triglycerides can also be produced by a two-step reaction as described in, for example, Japanese Patent Unexamined Published Application (hereinafter referred to as "J. P. KOKAI") No. 2000-270885.

(3) In the first reaction, glycerol and a highly unsaturated fatty acid or a lower alcohol ester thereof is reacted with lipase which is not position-specific to form a highly unsaturated fatty acid triglyceride under dehydration. In the second reaction, the highly unsaturated fatty acid triglyceride and a fatty acid having 12 or less carbon atoms or a lower alcohol ester thereof are reacted with a lipase specifically reactive on sn-1,3-positions to obtain the intended oil or fat having such a structure that the fatty acids bonded at the sn-1 position and sn-3 position have 12 or less carbon atoms and that at least 90% by mass of the fatty acids bonded at the sn-2 position are highly unsaturated fatty acids.

However, according to the method (1), it is difficult to obtain an oil or fat having a high MLM-type triglyceride content because various triglycerides (LML, MLL, LMM, MMM and LLL-type triglycerides) are also synthesized in addition to the MLM-type triglycerides. The term "LML-type triglycerides" indicates symmetric triglycerides having long-chain fatty acids at sn-1,3 positions and a medium chain fatty acid at sn-2 position. "MLL-type triglycerides" indicates asymmetric triglycerides having a medium chain fatty acid at sn-1 position and long chain fatty acids at sn-2,3 positions. "LMM-type triglycerides" indicates asymmetric triglycerides having a long-chain fatty acid at sn-1 position and medium chain fatty acids at sn-2 and 3 positions. "MMM-type triglycerides" indicates triglycerides having medium chain fatty acids at all of sn-1, 2 and 3 positions. "LLL-type triglycerides" indicates triglycerides having long chain fatty acids at all of sn-1, 2 and 3 positions.

In method (2), although it is possible to increase MLM-type triglyceride content by removing the fatty acid and ethyl esters of fatty acids after the completion of the reaction, it is impossible to effectively reuse those removed after the reaction and a high cost is necessitated in the practical production. Thus, symmetric triglycerides have not yet been generally and practically produced.

In method (2), both MLM-type triglyceride and MLL-type triglyceride are obtained after the completion of the reaction. However, it is practically impossible to fractionate these two kinds of triglycerides from each other because they are high-boiling oils or fats. For obtaining MLM-type triglyceride of a high purity by a method different from the fractionation, it is indispensable to use a large amount of ethyl ester of the medium chain fatty acid for the acidlysis reaction. As a result, the productivity is lowered to cause a serious increase in the cost.

In method (3), it is difficult to continuously conduct the first reaction because the enzyme cannot be fed into the column or the like since it is the dehydration reaction. Another defect of method (3) is that a quite excess amount of the lower alcohol ester must be subjected to the second reaction for obtaining the symmetric triglyceride of a high purity.

DISCLOSURE OF THE INVENTION

Therefore, the object of the present invention is to provide a method for producing MLM-type triglycerides of a high purity.

Another object of the present invention is to provide a method for efficiently producing MLM-type triglycerides of a high purity on an industrial scale while wastes formed in the course of the process are reduced in amount.

After intensive investigations made for the purpose of solving the above-described problems, the inventors have found that MLM-type triglycerides having a high purity can be obtained by conducting random transesterification reaction of specified starting materials in the step of the first reaction and then sn-1,3-specific transesterification reaction in the step of the second reaction.

Namely, the present invention provides a method for producing symmetric triglycerides, which comprises the steps of reacting a medium chain fatty acid triglyceride with a long chain fatty acid triglyceride in the presence of an enzyme or a chemical catalyst to conduct random transesterification reaction and thereby to obtain a reaction product containing a triglyceride composed of a medium chain fatty acid and a long chain fatty acid as the constituting fatty acids in the step of the first reaction; transesterifying the reaction product with an alcohol monoester of the medium chain fatty acid in the presence of an sn-1,3-position specific enzyme and then taking (a part or the whole of) the alcohol monoester of the medium chain fatty acid and the alcohol monoester of the long chain fatty acid out of the reaction product obtained by the second reaction to obtain the symmetric triglyceride composed of the medium chain fatty acids at the sn-1, 3 positions and the long chain fatty acid at the sn-2 position.

The present invention also provides the above-described method wherein the medium chain fatty acid triglyceride is (partially or wholly) taken out after the completion of the first reaction.

The present invention further provides the above-described method wherein the medium chain fatty acid triglyceride, the alcohol monoester of the medium chain fatty acid and the alcohol monoester of the long chain fatty acid are (partially or wholly) taken from the reaction product obtained by the second reaction, the medium chain fatty acid triglyceride taken out after the first and/or second reaction is recycled as the starting material for the first reaction, and the alcohol monoester of the medium chain fatty acid taken out after the second reaction is recycled as the starting material for the second reaction.

The present invention also provides a method for producing symmetric triglycerides, which comprises the steps of reacting a medium chain fatty acid triglyceride with an alcohol monoester of a long chain fatty acid in the presence of an enzyme or a chemical catalyst to conduct random transesterification reaction and thereby to obtain a reaction product containing a triglyceride composed of a medium chain fatty acid and a long chain fatty acid as the constituting fatty acids in the first reaction; obtaining a triglyceride-containing product by (partially or wholly) removing the alcohol monoester of the medium chain fatty acid, the alcohol monoester of the long chain fatty acid and the medium chain-fatty acid triglyceride from the reaction mixture; transesterifying the triglyceride-containing product with the alcohol monoester of the medium chain fatty acid in the presence of an sn-1,3-position specific enzyme and then taking out (a part or the whole of) the alcohol monoester of the medium chain fatty acid and the alcohol monoester of the long chain fatty acid from the reaction mixture obtained by the second reaction to obtain the symmetric triglyceride composed of the medium chain fatty acids at the sn-1, 3 positions and the long chain fatty acid at the sn-2 position.

The present invention also provides the above-described method wherein the medium chain fatty acid triglyceride is (partially or wholly) taken out after the completion of the second reaction.

The present invention also provides the above-described method wherein the medium chain fatty acid triglyceride taken out after the second reaction is recycled as the starting material in the first reaction.

The present invention also provides the above-described method wherein the alcohol monoester of the long chain fatty acid taken out after the second reaction is recycled as the starting material in the first reaction.

The present invention also provides the above-described method wherein the alcohol monoester of the medium chain fatty acid taken out after the second reaction is recycled as the starting material in the second reaction.

The present invention also provides the above-described method wherein the medium chain fatty acid triglyceride taken out after the first reaction is recycled as the starting material in the first reaction.

The present invention also provides the above-described method wherein the alcohol monoester of the long chain fatty acid taken out after the first reaction is recycled as the starting material in the first reaction.

The present invention also provides the above-described method wherein the alcohol monoester of the medium chain fatty acid taken out after the first reaction is recycled as the starting material in the second reaction.

The present invention also provides the above-described method wherein the alcohol monoester of the long chain fatty acid and medium chain fatty acid triglyceride taken out after the first reaction and/or second reaction are recycled as the starting materials in the first reaction, and the alcohol monoester of the medium chain fatty acid taken out after the first reaction and/or the second reaction is recycled as the starting material in the second reaction.

The present invention also provides a method for producing a symmetric triglyceride, which comprises the steps of reacting (a) a medium chain fatty acid triglyceride with (b) at least one member selected from the group consisting of a long chain fatty acid triglyceride, an alcohol monoester of a long chain fatty acid and a long chain fatty acid in the presence of an enzyme or a chemical catalyst to conduct random transesterification reaction and thereby to obtain the first reaction product containing a triglyceride composed of a medium chain fatty acid and a long chain fatty acid as the constituting fatty acids by the first reaction; transesterifying the first triglyceride in the reaction mixture with (c) at least one member selected from the group consisting of alcohol monoester of the medium chain fatty acid and the medium chain fatty acid in the presence of an sn-1,3-position specific enzyme to obtain the symmetric triglyceride composed of the medium chain fatty acid at the sn-1, 3 positions and the long chain fatty acid at the sn-2 position.

The present invention also provides the above-described method wherein the long chain fatty acid is a long chain unsaturated fatty acid.

The present invention also provides the above-described method wherein the long chain unsaturated fatty acid is one or more fatty acids selected from the group consisting of fatty acids having 18 carbon atoms, EPA (eicosapentaenoic acid) and DHA (docosahexaenoic acid).

The present invention also provides the above-described method wherein the enzyme used for the first reaction and/or the second reaction is powdery lipase at least 90 mass % of which has a particle diameter of 1 to 100 μm and the enzymatic reaction is carried out in the absence of solvent and in anhydrous system.

The present invention also provides the above-described method wherein the first and/or second enzymatic reaction is carried out by sealing the powdery lipase and a filter aid into a filter and passing the starting materials through the filter.

BEST MODE FOR CARRYING OUT THE INVENTION

Figure 1:
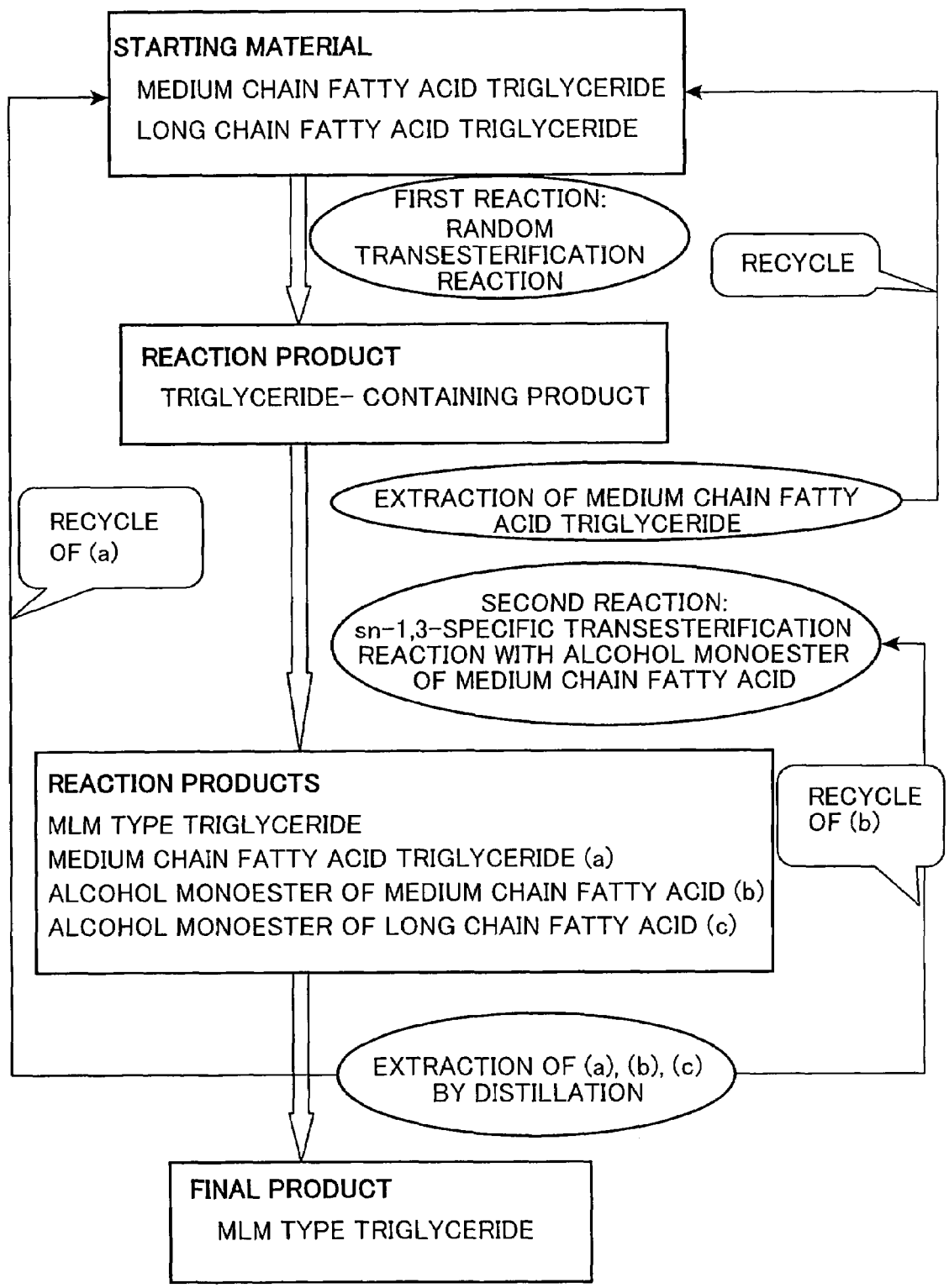
FIG. 1 is a flow chart schematically showing the method of the present invention for producing symmetric (MLM type) triglycerides from a medium chain fatty acid triglyceride and a long chain fatty acid triglyceride.

The term "medium chain fatty acid triglycerides" in the present invention means triglycerides in which fatty acids are medium fatty acids having 2 to 12, preferably 8 to 10 carbon atoms. The medium chain fatty acid triglycerides can be obtained by the dehydration synthesis reaction of glycerol and one or more medium chain fatty acids in the absence of any catalyst or by the transesterification reaction of glycerol and one or more alcohol esters of medium chain fatty acids. The medium chain fatty acid triglycerides can also be synthesized by using an enzyme such as lipase as a catalyst in the dehydration synthesis reaction or transesterification reaction.

The medium chain fatty acids may be either saturated fatty acids or unsaturated fatty acids. They include, for example, decanoic acid and octanoic acid.

The medium chain fatty acid triglycerides composed of those medium chain fatty acids can easily be obtained on the market. Those available on the market are, for example, ODO (a product of Nisshin OilliO Co., Ltd.).

In the long chain fatty acid triglycerides used in the present invention, the fatty acids are long chain fatty acids having 14 to 28 carbon atoms, preferably 16 to 22 carbon atoms and more preferably 16 to 18 carbon atoms. The long chain fatty acid triglycerides can be obtained by, for example, the dehydration synthesis reaction of glycerol and one or more long chain fatty acids in the absence of any catalyst or the transesterification reaction of glycerol and one or more alcohol esters of long chain fatty acids. The long chain fatty acid triglycerides can also be synthesized by using an enzyme as a catalyst in the dehydration synthesis reaction or transesterification reaction.

The long chain fatty acids may be either saturated fatty acids or unsaturated fatty acids. The long chain fatty acids having 14 to 28 carbon atoms are, for example, myristic acid, palmitic acid, stearic acid, arachidic acid, behenic acid, lignoceric acid, cerotic acid, myristoleic acid, pentadecenoic acid, palmitoleic acid, hexadecatrienoic acid, heptadecenoic acid, oleic acid, linoleic acid, linolenic acid, γ-linolenic acid, octadecatetraenoic acid, eicosenoic acid, eicosadienoic acid, eicosatrienoic acid, eicosatetraenoic acid, arachidonic acid, eicosapentaenoic acid (EPA), docosenoic acid, docosadienoic acid, docosapentaenoic acid and docosahexaenoic acid (DHA). Among them, long chain fatty acids having 16 to 22 carbon atoms are preferred.

The long chain fatty acids are preferably long chain unsaturated fatty acids because the latter has a low melting point and is easy to be operated. From the viewpoints of the use for general purpose and the functional property, one or more fatty acids selected from the group consisting of unsaturated fatty acids having 18 carbon atoms, EPA and DHA are preferred.

The long chain fatty acid triglycerides constituting the above-described long-chain fatty acids are easily available on the market. Those available on the market are, for example, soybean oil, rapeseed oil, rapeseed oil rich in oleic acid, sesame oil, corn oil, cotton seed oil, safflower oil, safflower oil rich in oleic acid, sunflower oil, sunflower oil rich in oleic acid, cacao oil, rice bran oil, peanut oil, olive oil, perilla oil, linseed oil, grape seed oil, macadamia nut oil, hazelnut oil, pumpkin seed oil, walnut oil, camellia oil, tea seed oil, borage oil, cotton seed oil, wheat germ oil, algae oil, beef tallow, hog fat, chicken oil, fish oil, lard and seal oil as well as those oils and fats having a degree of saturation lowered by the quality improvement and also hydrogenated products of those oils and fats. Among them, those having a high EPA and/or DHA content include, for example, fish oil.

The alcohol monoesters of the long chain fatty acids used in the present invention are esters of a long chain fatty acid having 14 to 28 carbon atoms, preferably 16 to 22 carbon atoms and more preferably 20 to 22 carbon atoms and an alcohol having 1 to 28 carbon atoms, preferably 1 to 4 carbon atoms. The alcohols constituting the alcohol monoesters of the long chain fatty acids are monohydric alcohols having one hydroxyl group. The alcohols may be primary, secondary and tertiary alcohols, and also they may be saturated aliphatic alcohols and unsaturated aliphatic alcohols. The alcohols constituting the alcohol monoesters of the long chain fatty acids are, for example, methanol, ethanol, propanol, isopropanol and butanol. Alcohols having 1 to 4 carbon atoms are preferred. In particular, ethanol is preferred from the viewpoint of the safety. The long chain fatty acids having 14 to 28 carbon atoms include those listed above.

The alcohol monoesters of the long chain fatty acids can be obtained by, for example, the alcoholysis reaction of animal and vegetable oils in the presence of an acid and an alkali catalyst in ethanol. The alcohol monoesters of the long chain fatty acids are also easily available on the market. Those available on the market are, for example, DHA-90E (ethyl docosahexanoate) of Nippon Chemical Feed Co., Ltd and EPA-90E (ethyl eicosapentaenoate) of Nippon Chemical Feed Co., Ltd.

The long chain fatty acids and medium chain fatty acids used in the present invention include those described above with reference to the long chain fatty acid triglycerides and medium chain fatty acid triglycerides.

The random transesterification reaction is conducted in the presence of an enzyme or a chemical catalyst in the present invention. When the fatty acid constituting the reactant is a highly unsaturated fatty acid, the enzyme is desirable because a side reaction is caused by the chemical catalyst.

When the random transesterification reaction is carried out in the presence of the enzyme, the enzyme is preferably an unspecific lipase. The unspecific lipases may be those obtained from animals, vegetables and microorganisms such as *Candida cylindraceae, Alcaligenes* sp. and *Alcaligenes faecalis*.

The enzyme, preferably lipase, is usable in the form of a powder or in immobilized form. For further increasing the reaction efficiency, it is most preferred to use a powdery lipase in which at least 90% of the powder particles have a diameter of 1 to 100 μm.

The diameter of the enzyme powder particles can be determined with, for example, laser-type particle size distribution meter LA-500 of HORIBA Co. The powdery enzymes in which 90% of the powder particles have a diameter of 1 to 100 μm include, for example, Lipase QLM (Meito Sangyo Co., Ltd.).

The amount of the enzyme to be used for the random transesterification reaction is preferably 0.01 to 20 mass %, more preferably 0.1 to 5 mass %, based on the whole starting materials.

When the enzyme is used, the reaction temperature is preferably 20 to 100° C., more preferably 40 to 80° C., from the viewpoint of the durability thereof.

When a chemical catalyst is used for the random transesterification reaction, the catalysts usable herein include, for example, alkaline chemical catalysts such as sodium methylate and acid chemical catalysts such as sulfuric acid. They are easily available on the market. For example, commercially available sodium methylate includes "Sodium Methylate" (Nippon Soda Co., Ltd.) and sodium methoxide (Wako Pure Chemical Industries, Ltd.). The amount of the chemical catalyst used for the reaction is preferably 0.10 to 5 mass %, more preferably 0.1 to 2 mass %, based on the whole starting materials.

When the chemical catalyst is used, the reaction time is preferably 0.5 to 20 hours, more preferably 2 to 5 hours.

In the transesterification reaction carried out in the presence of sn-1,3-position-specific enzyme in the present invention, the specificity resides in sn-1,3-positions of triglycerides. The sn-1,3 position-specific enzymes are, for example, porcine pancreas lipase, lipase derived from soybeans, rice bran, castor beans or the like, *Aspergillus niger, Rhizopus delemar, Rhizopus javanicus, Mucor miehei* and *Pseudomonas fluorescens*.

The sn-1,3-position specific enzymes, preferably lipase, are(is) usable in the form of a powder or after the immobilization. Those enzymes are, for example, Lipase PL (Meito Sangyo Co., Ltd.), lipozyme TL (Novo) and an enzyme powder from *Rhizomucor miehei*. The powdery enzymes usable herein include powdery lipase at least 90% of the particles of which have a diameter of 1 to 100 µm. The particle diameter of the powdery enzymes can be determined by the above-described method.

The amount of the sn-1,3-position specific enzyme is preferably 0.01 to 10 mass %, more preferably 0.1 to 5 mass %, based on the whole starting materials.

When the sn-1,3-position specific enzyme is used, the reaction temperature is preferably 20 to 90° C., more preferably 30 to 60° C., from the viewpoint of the durability thereof.

The random transesterification reaction with the enzyme and the transesterification reaction with sn-1,3-position specific enzyme is preferably carried out in the absence of any solvent under anhydrous condition from the viewpoint of the workability. In view of the efficiency, the enzymatic reaction is preferably carried out by sealing the powdery lipase and a filter aid into a filter and passing the starting materials through the filter. This process is effective for separating the reaction products from the enzyme remaining after the reaction. The time required for the batchwise random transesterification reaction or sn-1,3-specific transesterification reaction will be described in detail below.

The method of the present invention for producing symmetric triglycerides, in particular, MLM-type triglycerides from a medium-chain fatty acid triglyceride and a long chain fatty acid triglyceride will be described in order below. FIG. 1 is a flow chart schematically showing the method for producing the symmetric triglycerides.

As the first reaction in the method for producing the symmetric triglycerides, the random transesterification reaction of the medium chain fatty acid triglyceride and the long chain fatty acid triglyceride is carried out in the presence of the enzyme or the chemical catalyst. When the reaction is carried out batchwise in the presence of the enzyme, the reaction time is preferably 1 to 50 hours, more preferably 15 to 25 hours.

Although the mixing mass ratio of the medium chain fatty acid triglyceride to the long chain fatty acid triglyceride used as the starting materials in the first reaction is not particularly limited, the mixing mass ratio is preferably 1:9 to 9:1, more preferably 1:4 to 1:1 in order to control the relative amount of the long chain fatty acid triglyceride in the reaction product and to obtain a high reaction efficiency.

After the random transesterification reaction of the medium chain fatty acid triglyceride and the long chain fatty acid triglyceride in the first reaction step, triglycerides of LML, MLL, LMM, MMM and LLL types are obtained in addition to the MLM triglyceride comprising the medium chain fatty acid at the sn-1,3 positions and the long chain fatty acid at the sn-2 position.

When the proportion of the medium chain fatty acid triglyceride to the long chain fatty acid triglyceride in the starting materials is over the above-described range in the first reaction step, the reaction mixture obtained after the first reaction contains a large amount of LLL-type triglyceride. As a result, a large amount of the alcohol monoester of the medium chain fatty acid is required for obtaining the intended MLM-type triglyceride by the second reaction. In this case, a problem of lowering the reaction efficiency occurs.

It is preferred that the medium chain fatty acid triglyceride (MMM type) is (partially or wholly) removed from the reaction mixture after the random transesterification reaction of the medium chain fatty acid triglyceride and the long chain fatty acid triglyceride in the first reaction step. After the removal in this step, the medium chain fatty acid triglyceride content of the triglycerides is preferably 0 to 10 mass %, more preferably 0 to 6 mass % and most preferably 0 to 3 mass %. The medium chain fatty acid triglyceride (MMM type) can be separated from other triglycerides by distillation method wherein the mixture can be divided into a fraction (having a high medium chain fatty acid triglyceride content) which distills at 200° C. and 30 Pa and the remaining fraction (having a high content of other triglycerides). The distillation methods are, for example, batchwise, continuous, thin film and falling film distillation methods.

The medium chain fatty acid triglyceride taken out by the distillation method is efficiently reusable as the starting material for the first reaction.

The reaction mixture obtained after the first reaction or a triglyceride-containing mixture obtained by (partially or wholly) removing the medium chain fatty acid triglyceride from the reaction mixture is transesterified with the alcohol monoester of the medium chain fatty acid in the presence of the sn-1,3-position specific enzyme in the second reaction step. When the transesterification reaction is carried out by the batchwise method, the reaction time is preferably 1 to 50 hours, more preferably 15 to 30 hours.

The proportion (by mass) of the (first) triglyceride comprising the medium chain fatty acid and the long chain fatty acid as the constituent fatty acids to the alcohol monoester of the medium chain fatty acid and/or the medium chain fatty acid in the second reaction is preferably 1:0.5 to 1:20, more preferably 1:2 to 1:7.

By removing the alcohol monoester of the medium chain fatty acid and the alcohol monoester of the long chain fatty acid after the second reaction, the purity of the MLM type triglyceride in the final product can be increased. Further, it is also preferred to also remove the medium chain fatty acid triglyceride. These substances can be removed by the distillation process such as batchwise distillation.

The removal of the alcohol monoester of the medium chain fatty acid, the alcohol monoester of the long chain fatty acid and the medium chain fatty acid triglyceride from the reaction mixture obtained after the second reaction is preferably conducted for reducing the contents of them in the triglyceride-containing reaction mixture obtained after the removal so as to increase the symmetric triglyceride content in the final product.

Concretely, the amount of the alcohol monoester of the medium chain fatty acid in the triglyceride-containing product obtained after this removing process is preferably 0 to 5 mass %, more preferably 0 to 3 mass % and most preferably 0 to 1 mass %. The amount of the alcohol monoester of the long chain fatty acid in the triglyceride-containing product obtained after this removing process is preferably 0 to 5 mass %, more preferably 0 to 3 mass % and most preferably 0 to 1 mass %. The amount of the medium chain fatty acid triglyceride in the triglyceride-containing product obtained after this removing process is preferably 0 to 15 mass %, more preferably 0 to 10 mass % and most preferably 0 to 8 mass %.

However, when a mixture of the symmetric triglyceride and the medium chain fatty acid triglyceride is to be obtained as the final product, it is unnecessary to remove the medium chain fatty acid triglyceride from the triglyceride-containing mixture to the above-described extent. In this case, only the alcohol monoester of the medium chain fatty acid and the alcohol monoester of the long chain fatty acid are removed in such amounts that the contents of them in the triglyceride-containing mixture will be as described above.

The alcohol monoester of the medium chain fatty acid, the alcohol monoester of the long chain fatty acid and the medium chain fatty acid triglyceride are preferably taken out from the reaction mixture obtained after the second reaction in two different fractions, i. e. a fraction having a high content of the alcohol monoester of the medium chain fatty acid and a fraction having a high content of the medium chain fatty acid triglyceride and the alcohol monoester of the long chain fatty acid. The fractionation can be conducted by controlling the distillation temperature, degree of reduction of the pressure and distillation time. For example, the reaction mixture can be divided into a fraction (having a high content of the alcohol monoester of the medium chain fatty acid) which is distilled in the former half of the distillation (50° C., 100 Pa) and a fraction (having a high content of the medium chain fatty acid triglyceride and the alcohol monoester of the long chain fatty acid) which is distilled in the latter half of the distillation (230° C., 1 Pa).

The reaction mixture can be taken out after dividing it into 3 fractions, i. e. a fraction having a high content of the alcohol monoester of the medium chain fatty acid, a fraction having a high content of the alcohol monoester of the long chain fatty acid and a fraction having a high medium chain fatty acid triglyceride content. The fractionation can be conducted by controlling the distillation temperature, degree of reduction of the pressure and distillation time. For example, the reaction mixture can be divided into a fraction (having a high content of the alcohol monoester of the medium chain fatty acid) which is distilled in the former stage of the distillation (25° C., 30 Pa), a fraction (having a high content of the alcohol monoester of the long chain fatty acid) which is distilled in the middle stage of the distillation (180° C., 1 Pa) and a fraction (having a high content of the medium chain fatty acid triglyceride) which is distilled in the latter stage of the distillation (230° C., 1 Pa).

The medium chain fatty acid triglyceride taken out after the second reaction is reusable as the starting material for the first reaction. The alcohol monoester of the medium chain fatty acid taken out after the second reaction is also reusable as the starting material for the second reaction. The alcohol monoester of the long chain fatty acid taken out after the second reaction is reusable as the starting material for the first reaction in a method of the present invention for producing the symmetric triglyceride from the medium chain fatty acid triglyceride and the alcohol monoester of the long chain fatty acid as will be described below.

Thus, the method of the present invention for producing symmetric (MLM type) triglyceride from the medium chain fatty acid triglyceride and the long chain fatty acid triglyceride is efficient because all by-products other than the intended MLM type triglyceride can be used.

Figure 2:
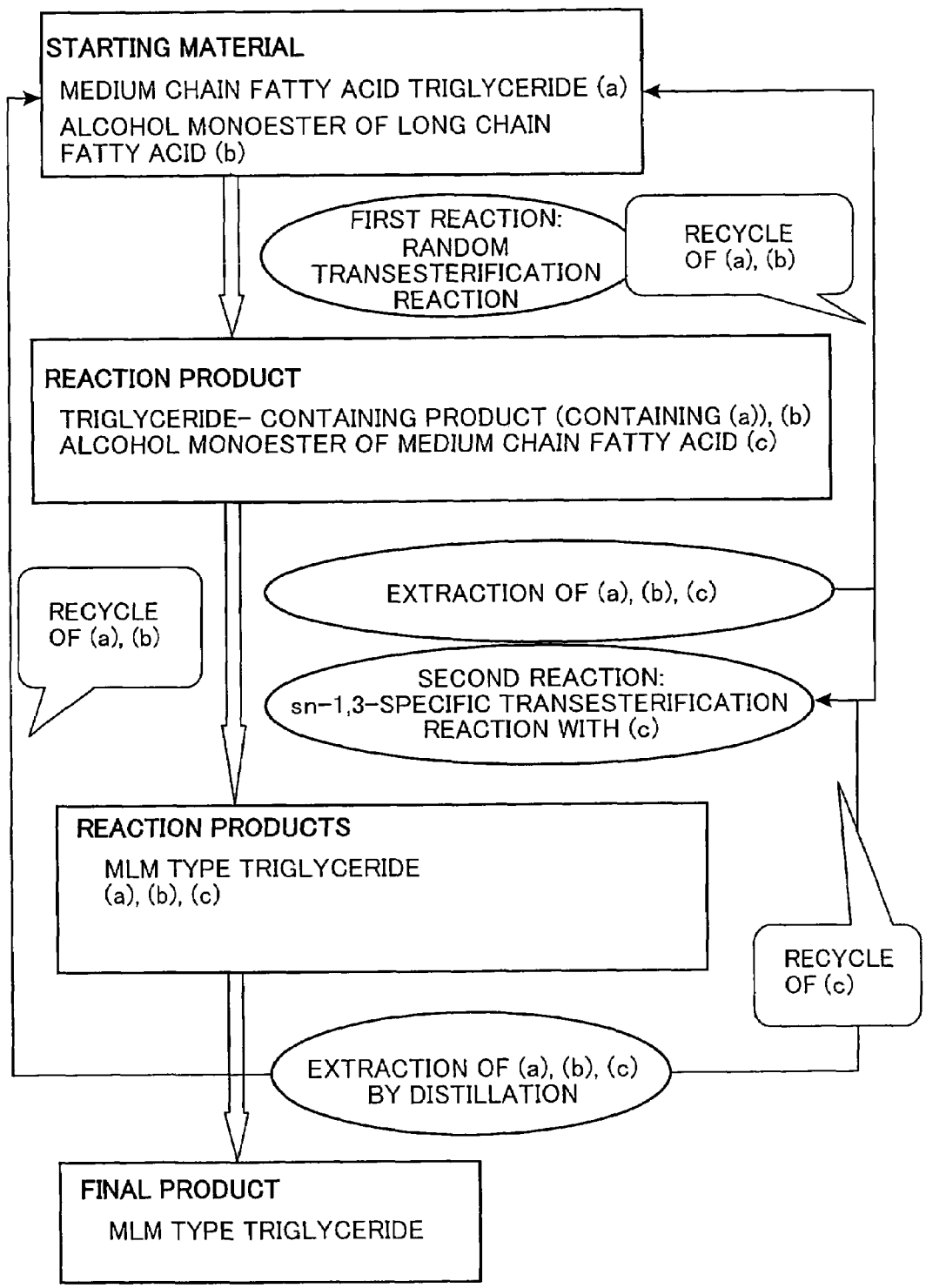
FIG. 2 is a flow chart schematically showing the method of the present invention for producing symmetric (MLM type) triglycerides from a medium chain fatty acid triglyceride and an alcohol monoester of a long chain fatty acid.

The method of the present invention for producing symmetric MLM-type triglycerides from the medium chain fatty acid triglyceride and the alcohol monoester of the long chain fatty acid will be described in order below. FIG. 2 is a flow chart schematically showing the method for producing the symmetric triglycerides.

In the method for producing symmetric triglycerides, the random transesterification reaction, i. e. the first reaction, of the medium chain fatty acid triglyceride and the alcohol monoester of the long chain fatty acid is carried out in the presence of the enzyme or the chemical catalyst. The alcohol monoester of the long chain fatty acid used herein may be that obtained as a by product in the above-described production of the symmetric triglyceride from the medium chain fatty acid triglyceride and the long chain fatty acid triglyceride. When the random transesterification reaction is carried out batch-wise in the presence of the enzyme, the reaction time is preferably 1 to 100 hours, more preferably 15 to 80 hours.

Although the mixing mass ratio of the medium chain fatty acid triglyceride to the alcohol monoester of the long chain fatty acid used as the starting materials for the first reaction is not particularly limited, it is preferably 8:1 to 1:8, more preferably 2:1 to 1:5 for lowering the relative amount of the long chain fatty acid triglyceride in the reaction product and for obtaining a high reaction efficiency. The preferred mixing mass ratio of them is the same as above when the alcohol monoester of the long chain fatty acid is replaced with the long chain fatty acid.

When the random transesterification reaction of the medium chain fatty acid triglyceride and the alcohol monoester of the alcohol monoester of the long chain fatty acid is carried out in the step of the first reaction, the obtained reaction mixture comprises LML, MLL, LMM, MMM and LLL-type triglyceride, the alcohol monoester of the long chain fatty acid and alcohol monoester of the medium chain fatty acid in addition to the MLM-type triglyceride having medium-chain fatty acid at the 1,3 positions and a long chain fatty acid at the 2 position.

When the proportion of the medium chain fatty acid triglyceride to the alcohol monoester of the long chain fatty acid used as the starting materials is higher than the above-described range in the first reaction, the reaction mixture obtained after completion of the first reaction contains a large amount of the LLL-type triglyceride. In this case, a large amount of the alcohol monoester of the medium chain fatty acid is required for obtaining the intended MLM-type triglyceride to reduce the reaction efficiency in the second reaction as will be described below.

For enhancing the reaction efficiency in the second reaction which will be described below, a part or the whole of the alcohol monoester of the medium chain fatty acid, the alcohol monoester of the long chain fatty acid and the medium chain fatty acid triglyceride is taken out from the reaction mixture obtained in the first reaction step by, for example, the batch-wise distillation. In this case, the amount of the substances in the triglyceride-containing mixture after the removing process is desirably small.

Concretely, after the removing process, the amount of the alcohol monoester of the medium chain fatty acid in the triglyceride-containing mixture is preferably 0 to 5 mass %, more preferably 0 to 3 mass % and most preferably 0 to 2 mass %. After this process, the amount of the alcohol monoester of the long chain fatty acid in the triglyceride-containing mixture is preferably 0 to 5 mass %, more preferably 0 to 3 mass % and most preferably 0 to 2 mass %. After the removing process, the amount of the medium chain fatty acid triglyceride in the triglyceride-containing mixture is preferably 0 to 15 mass %, more preferably 0 to 10 mass % and most preferably 0 to 8 mass %.

The alcohol monoester of the medium chain fatty acid, the alcohol monoester of the long chain fatty acid and the medium chain fatty acid triglyceride are preferably taken out from the reaction mixture obtained after the first reaction step in two different fractions, i. e. a fraction having a high content of the alcohol monoester of the medium chain fatty acid and a fraction having a high content of the alcohol monoester of the long chain fatty acid and the medium chain fatty acid triglyceride, from the viewpoint of the reuse of them as the starting materials. The fractionation can be conducted by controlling the distillation temperature, degree of reduction of the pressure and distillation time. For example, the reaction mixture can be divided into a fraction (having a high content of the alcohol monoester of the medium chain fatty acid) which is distilled in the former half of the distillation (50° C., 100 Pa) and a fraction (having a high content of the alcohol monoester of the medium chain fatty acid) which is distilled in the latter half of the distillation (230° C., 1 Pa).

The reaction mixture can be taken out after dividing it into 3 fractions, i. e. a fraction having a high content of the alcohol monoester of the medium chain fatty acid, a fraction having a high content of the alcohol monoester of the long chain fatty acid and a fraction having a high medium chain fatty acid triglyceride content. The fractionation can be conducted by controlling the distillation temperature, degree of reduction of the pressure and distillation time. For example, the reaction mixture can be divided into a fraction (having a high content of the alcohol monoester of the medium chain fatty acid) which is distilled in the former stage of the distillation (25° C., 30 Pa), a fraction (having a high content of the alcohol monoester of the long chain fatty acid) which is distilled in the middle stage of the distillation (180° C., 1 Pa) and a fraction (having a high content of the medium chain fatty acid triglyceride) which is distilled in the latter stage of the distillation (230° C., 1 Pa).

The alcohol monoester of the long chain fatty acid and the medium chain fatty acid triglyceride taken out after the first reaction are reusable as the starting materials in the first reaction step. The alcohol monoester of the medium chain fatty acid taken out after the first reaction is efficiently reusable as the starting material for the second reaction.

Then the triglyceride-containing reaction mixture from which the medium chain fatty acid triglyceride, the alcohol monoester of the medium chain fatty acid and the alcohol monoester of the long chain fatty acid have (partially or wholly) been taken out is transesterified with the alcohol monoester of the medium chain fatty acid in the presence of the above-described sn-1,3 position specific enzyme. When the transesterification reaction is carried out batchwise, the reaction time is preferably 1 to 100 hours, more preferably 15 to 80 hours.

The proportion (by mass) of the (first) triglyceride comprising the medium chain fatty acid and the long chain fatty acid as the constituent fatty acids to the alcohol monoester of the medium chain fatty acid and/or the medium chain fatty acid in the second reaction step is preferably 1:0.5 to 1:20, more preferably 1:2 to 1:7.

By removing the alcohol monoester of the medium chain fatty acid and the alcohol monoester of the long chain fatty acid after the second reaction in the same manner as that in the above-described second reaction in the process for producing the symmetric triglyceride from the medium chain fatty acid triglyceride and the long chain fatty acid triglyceride, the purity of the MLM type triglyceride in the final product can be increased. Further, the purity of the MLM type triglyceride can be increased also by removing the medium chain fatty acid triglyceride. Methods for removing them are as described above. It is also possible to obtain a mixture of the MLM type triglyceride and the medium chain fatty acid triglyceride as the final product.

The medium chain fatty acid triglyceride and the alcohol monoester of the long chain fatty acid taken out after the second reaction are reusable as the starting materials in the first reaction step. Also the alcohol monoester of the medium chain fatty acid taken out after the second reaction is reusable as the starting material in the second reaction.

Thus, the method of the present invention for producing the symmetric (MLM type) triglycerides from the medium chain fatty acid triglyceride and the alcohol monoester of the long chain fatty acid is efficient because all by-products other than the intended MLM type triglyceride can be effectively used.

In the method of the present invention for producing the symmetric MLM-type triglycerides from the medium chain fatty acid triglyceride and the long chain fatty acid, the symmetric triglyceride of a high purity can be efficiently produced by removing components other than the triglyceride comprising the medium chain fatty acid and the long chain fatty acid as the constituent fatty acids and triglyceride comprising the long chain fatty acid as the constituent fatty acid after the first reaction and also removing the components other than the intended symmetric triglyceride comprising the medium chain fatty acid at sn-1,3 positions and the long chain fatty acid at sn-2 position after the second reaction.

Further, in the components taken out after the first reaction, those which are the same as the starting materials used in the first reaction can be recycled as the starting materials for the first reaction and also those which are the same as the starting materials used in the second reaction can be recycled as the starting materials for the second reaction. In addition, in the components taken out after the second reaction, those which are the same as the starting materials used in the first reaction can be recycled as the starting materials for the first reaction and also those which are the same as the starting materials used in the second reaction can be recycled as the starting materials for the second reaction.

The detailed description will be made below with reference to a case wherein a symmetric triglyceride is produced from the medium chain fatty acid triglyceride and the long chain fatty acid as the starting materials.

After the completion of the first reaction, the medium chain fatty acid triglyceride, the long chain fatty acid and the medium chain fatty acid are taken out of the reaction product to obtain the triglyceride-containing mixture. The second reaction is carried out by using the triglyceride-containing mixture and the medium chain fatty acid as the starting materials. After the completion of the second-reaction, the medium chain fatty acid triglyceride, long chain fatty acid and the medium chain fatty acid are taken out of the reaction product to obtain the symmetric triglyceride comprising the medium chain fatty acid at sn-1,3 positions and the long chain fatty acid at sn-2 position. The medium chain fatty acid triglyceride and the long chain fatty acid taken out after the completion of the first reaction and the second reaction can be recycled as the starting materials for the first reaction, and the medium chain fatty acid taken out after the completion of the first reaction and the second reaction can be recycled as the starting materials for the second reaction.

As described above, long chain unsaturated fatty acid triglycerides, long chain fatty acid monoesters and long chain fatty acids are preferably unsaturated ones because they have a low melting point and they are easy to be operated. However, the symmetric triglycerides comprising the long chain saturated fatty acid as a constituent fatty acid can also be obtained after an additional process of the hydrogenation.

Namely, the symmetric triglyceride comprising the saturated long chain fatty acid as the constituting fatty acid can be obtained by hydrogenating the symmetric triglyceride, comprising the unsaturated fatty acid as the constituent fatty acid, obtained by the present invention. In this process, the operation is easy because the saturated long chain fatty acid triglyceride, the monoester of the saturated long chain fatty acid or the saturated long chain fatty acid each having a high melting point is not used as the starting material in the steps of the reaction and purification.

Concretely, a symmetric triglyceride comprising octanoic acid at sn-1,3 positions and stearic acid at sn-2 position as the constituting fatty acids can be obtained by the hydrogenation of the symmetric triglyceride comprising octanoic acid at sn-1,3 positions and oleic acid at sn-2 position, which is produced by the present invention. The hydrogenation can be conducted by a well-known method.

Thus obtained symmetric triglyceride comprising octanoic acid at sn-1,3 positions and stearic acid at sn-2 position is suitable for use as a substitute fat for chocolates.

EXAMPLES

The following Examples will further illustrate the present invention, which by no means limit the invention. In the Examples, DHA ethyl ester indicates ethyl docosahexaenoate and EPA ethyl ester indicates ethyl eicosapentaenoate.

Example 1

Production of Symmetric Triglyceride of DHA Comprising Octanoic Acid at sn-1,3 Positions and DHA at sn-2 Position:

<The First Reaction>

500 g of tricaprylin (trade name: Tricaprylin, Sigma Aldrich Japan Co.), 500 g of DHA ethyl ester (trade name: DHA-90E, Nippon Chemical Feed Co., Ltd.) and 20 g of unspecific lipase (trade name: Lipase QLM, Meito Sangyo Co., Ltd.) were fed into a 2000 ml reaction flask. After the enzymatic reaction carried out under stirring with a propeller at 50° C. for 72 hours, 980 g of the reaction product was obtained. After the completion of the reaction, ethyl octanoate, DHA ethyl ester and tricaprylin were taken out of the reaction product with a centrifugal molecular distillation device (Nippon Sharyo Ltd.) to obtain 350 g of the triglyceride-containing reaction product. The respective components were taken out by the film distillation under the following conditions:

(1) Former step in the distillation: 25° C., 30 Pa; component (A) 150 g
(2) Middle step in the distillation: 180° C., 1 Pa; component (B) 270 g
(3) Latter step in the distillation: 230° C., 1 Pa; component (C) 200 g.

The components (A) to (C) were analyzed by GLC (6890 Series GC System of Agilent Technologies, Inc.) to find that the main components were as follows:
(A) Ethyl octanoate content: 99 mass %
(B) DHA ethyl ester content: 93 mass %
(C) Tricaprylin content: 98 mass %.

<The Second Reaction>

350 g of the triglyceride-containing reaction mixture obtained as described above, 1750 g of ethyl octanoate (trade name: Ethyl Octanoate, Inoue Perfumery Co., Ltd.) and 40 g of sn-1,3-position specific lipase (trade name: Lipozyme TL, NOVO) were fed into a 5000 ml reaction flask. After the enzymatic reaction carried out under stirring with a propeller at 50° C. for 72 hours, 2000 g of the reaction mixture was obtained. After the completion of the reaction, ethyl octanoate, DHA ethyl ester and tricaprylin were taken out of the reaction mixture with a centrifugal molecular distillation device (Nippon Sharyo Ltd.) to obtain 130 g of the triglyceride-containing mixture. The respective components were taken out by the film distillation under the following conditions:

(4) Former step in the distillation: 25° C., 30 Pa; component (A') 1500 g
(5) Middle step in the distillation: 180° C., 1 Pa; component (B') 120 g
(6) Latter step in the distillation: 230° C., 1 Pa; component (C') 100 g.

The components (A') to (C') were analyzed by GLC to find that the main components were as follows:
(A') Ethyl octanoate content: 99 mass %
(B') DHA ethyl ester content: 90 mass %
(C') Tricaprylin content: 99 mass %.

After the completion of the second reaction, the triglyceride-containing reaction mixture from which ethyl octanoate, DHA ethyl ester and tricaprylin had been removed was analyzed by GLC and HPLC (LC-9A LIQUID CHOROMATOGRAPH of Shimadzu Corporation) to find that the amount of the symmetric triglyceride comprising octanoic acid at the sn-1, 3 positions and DHA at the sn-2 position was 93 mass %.

Example 2

Production of Symmetric Triglyceride Comprising Octanoic Acid at the sn-1, 3 Positions and DHA at the sn-2 Position by Using Ethyl Octanoate, DHA Ethyl Ester and Tricaprylin, Taken Out as Described Above, as the Starting Materials:

<The First Reaction>

1000 g of a mixture of the components (B), (C), (B') and (C') taken out in Example 1, tricaprylin (trade name: Tricaprylin, Sigma Aldrich Japan Co.) and DHA ethyl ester (trade name: DHA-90E, Nippon Chemical Feed Co., Ltd) in such a proportion that DHA ethyl ester content would be about 50 mass % and tricaprylin content would be about 50 mass %, and 20 g of Lipase QLM (Meito Sangyo Co., Ltd.) were fed into a 2000 ml reaction flask. After the enzymatic reaction carried out under stirring with a propeller at 50° C. for 72 hours, 980 g of the reaction mixture was obtained. After the completion of the reaction, ethyl octanoate, DHA ethyl ester and tricaprylin were taken out of the reaction mixture with a centrifugal molecular distillation device (Nippon Sharyo Ltd.) to obtain 350 g of the triglyceride-containing mixture.

The respective components were taken out by the film distillation under the following conditions:
(1) Former step in the distillation: 25° C., 30 Pa; component (D) 150 g
(2) Middle step in the distillation: 180° C., 1 Pa; component (E) 270 g
(3) Latter step in the distillation: 230° C., 1 Pa; component (F) 200 g.

The components (D) to (F) were analyzed by GLC to obtain the following results:
(D) Ethyl octanoate content: 99 mass %
(E) DHA ethyl ester content: 93 mass %
(F) Tricaprylin content: 98 mass %.

<The Second Reaction>

350 g of the triglyceride-containing reaction mixture obtained as described above, 1750 g of a mixture of components (A) and (A') taken out in Example 1 and ethyl octanoate (trade name: Ethyl Octanoate, Inoue Perfumery Co., Ltd.) and 40 g of sn-1,3-position specific lipase (trade name: Lipozyme TL, NOVO) were fed into a 5000 ml reaction flask. After the enzymatic reaction carried out under stirring with a propeller at 50° C. for 72 hours, 2000 g of the reaction mixture was obtained. After the completion of the reaction, ethyl octanoate, DHA ethyl ester and tricaprylin were taken out of the reaction mixture with a centrifugal molecular distillation device (Nippon Sharyo Ltd.) to obtain 130 g of the triglyceride-containing reaction mixture.

The respective components were taken out by the film distillation under the following conditions:
(4) Former step in the distillation: 25° C., 30 Pa; component (D') 1500 g
(5) Middle step in the distillation: 180° C., 1 Pa; component (E') 120 g
(6) Latter step in the distillation: 230° C., 1 Pa; component (F') 100 g.

The components (D') to (F') were analyzed by GLC to obtain the following results:
(D') Ethyl octanoate content: 99 mass %
(E') DHA ethyl ester content: 90 mass %
(F') Tricaprylin content: 99 mass %.

After the completion of the second reaction, the triglyceride-containing reaction mixture from which ethyl octanoate, DHA ethyl ester and tricaprylin had been removed was analyzed by GLC and HPLC to find that the amount of the symmetric triglyceride comprising octanoic acid at the sn-1, 3 positions and DHA at the sn-2 position was 91 mass %.

Example 3

Production of Symmetric Triglyceride Comprising Octanoic Acid at sn-1,3 Positions and EPA at sn-2 Position:

<The First Reaction>

500 g of tricaprylin (trade name: Tricaprylin, Sigma Aldrich Japan Co.), 500 g of EPA ethyl ester (trade name: EPA-90E, Nippon Chemical Feed Co., Ltd) and 20 g of Lipase QLM (Meito Sangyo Co., Ltd.) were fed into a 2000 ml reaction flask. After the enzymatic reaction carried out under stirring with a propeller at 50° C. for 72 hours, 980 g of the reaction mixture was obtained. After the completion of the reaction, ethyl octanoate, EPA ethyl ester and tricaprylin were taken out of the reaction mixture with a centrifugal molecular distillation device (Nippon Sharyo Ltd.) to obtain 350 g of the triglyceride-containing mixture.

The respective components were taken out by the film distillation under the following conditions:
(1) Former step in the distillation: 25° C., 30 Pa; component (G) 150 g
(2) Middle step in the distillation: 180° C., 1 Pa; component (H) 260 g
(3) Latter step in the distillation: 230° C., 1 Pa; component (I) 200 g.

The components (G) to (I) were analyzed by GLC to obtain the following results:
(G) Ethyl octanoate content: 99 mass %
(H) EPA ethyl ester content: 93 mass %
(I) Tricaprylin content: 98 mass %.

<The Second Reaction>

340 g of the triglyceride-containing reaction mixture obtained as described above, 1750 g of ethyl octanoate (trade name: Ethyl Octanoate, Inoue Perfumery Co., Ltd.) and 40 g of sn-1,3-position specific lipase (trade name: Lipozyme TL, NOVO) were fed into a 5000 ml reaction flask. After the enzymatic reaction carried out under stirring with a propeller at 50° C. for 72 hours, 2000 g of the reaction mixture was obtained. After the completion of the reaction, ethyl octanoate, EPA ethyl ester and tricaprylin were taken out of the reaction mixture with a centrifugal molecular distillation device (Nippon Sharyo Ltd.) to obtain 120 g of the triglyceride-containing reaction mixture. The respective components were taken out by the film distillation under the following conditions:
(4) Former step in the distillation: 25° C., 30 Pa; component (G') 1600 g
(5) Middle step in the distillation: 180° C., 1 Pa; component (H') 110 g
(6) Latter step in the distillation: 230° C., 1 Pa; component (I') 100 g.

The components (G') to (I') were analyzed by GLC to obtain the following results:
(G') Ethyl octanoate content: 99 mass %
(H') EPA ethyl ester content: 90 mass %
(I') Tricaprylin content: 99 mass %.

After the completion of the second reaction, the triglyceride-containing reaction mixture from which ethyl octanoate, EPA ethyl ester and tricaprylin had been removed was analyzed by GLC and HPLC to find that the amount of the symmetric triglyceride comprising octanoic acid at the sn-1, 3 positions and EPA at the sn-2 position was 93 mass %.

Example 4

Production of Symmetric Triglyceride Comprising Octanoic Acid at the sn-1, 3 Positions and EPA at the sn-2 Position by Using Ethyl Octanoate, EPA Ethyl Ester and Tricaprylin, Taken Out as Described Above, as the Starting Materials:

<The First Reaction>

1000 g of a mixture of the components (H), (I), (H') and (I') taken out in Example 3, tricaprylin (trade name: Tricaprylin, Sigma Aldrich Japan Co.) and EPA ethyl ester (trade name: EPA-90E, Nippon Chemical Feed Co., Ltd.) in such a proportion that tricaprylin content would be about 50 mass % and EPA ethyl ester content would be about 50 mass %, and 20 g of Lipase QLM (Meito Sangyo Co., Ltd.) were fed in to a 2000 ml reaction flask. After the enzymatic reaction carried out under stirring with a propeller at 50° C. for 72 hours, 980 g of the reaction mixture was obtained. After the completion of the reaction, ethyl octanoate, EPA ethyl ester and tricaprylin were taken out of the reaction mixture with a centrifugal molecular distillation device (Nippon Sharyo Ltd.) to obtain 350 g of the triglyceride-containing mixture.

The respective components were taken out by the film distillation under the following conditions:
(1) Former step in the distillation: 25° C., 30 Pa; component (J) 150 g
(2) Middle step in the distillation: 180° C., 1 Pa; component (K) 260 g
(3) Latter step in the distillation: 230° C., 1 Pa; component (L) 200 g.

The components (J) to (L) were analyzed by GLC to obtain the following results:
(J) Ethyl octanoate content: 99 mass %
(K) EPA ethyl ester content: 93 mass %
(L) Tricaprylin content: 98 mass %.

<The Second Reaction>

340 g of the triglyceride-containing mixture obtained as described above, 1750 g of a mixture of components (G) and (G') taken out in Example 3 and ethyl octanoate (trade name: Ethyl Octanoate, Inoue Perfumery Co., Ltd.) and 200 g of sn-1,3-position specific lipase (trade name: Lipozyme TL, NOVO) were fed into a 5000 ml reaction flask. After the enzymatic reaction carried out under stirring with a propeller at 50° C. for 72 hours, 2000 g of the reaction mixture was obtained. After the completion of the reaction, ethyl octanoate, EPA ethyl ester and tricaprylin were taken out of the reaction mixture with a centrifugal molecular distillation device (Nippon Sharyo Ltd.) to obtain 120 g of the triglyceride-containing mixture.

The respective components were taken out by the film distillation under the following conditions:
(4) Former step in the distillation: 25° C., 30 Pa; component (J') 1500 g
(5) Middle step in the distillation: 180° C., 1 Pa; component (K') 120 g
(6) Latter step in the distillation: 230° C., 1 Pa; component (L') 100 g.

The components (J') to (L') were analyzed by GLC to obtain the following results:
(J') Ethyl octanoate content: 99 mass %
(K') EPA ethyl ester content: 90 mass %
(L') Tricaprylin content: 99 mass %.

After the completion of the second reaction, the triglyceride-containing reaction mixture from which ethyl octanoate, EPA ethyl ester and tricaprylin had been removed was analyzed by GLC and HPLC to find that the amount of the symmetric triglyceride comprising octanoic acid at the sn-1, 3 positions and EPA at the sn-2 position was 91 mass %.

Example 5

Production of Symmetric Triglyceride Comprising Medium Chain Fatty Acids at sn-1,3 Positions and Unsaturated Fatty Acid having 18 Carbon Atoms at sn-2 Position:

<The First Reaction>

700 g of High Oleic castor oil (trade name: Olein Rich, Showa Sangyo Co., Ltd.), 300 g of medium chain fatty acid triglycerides (trade name: ODO, Nisshin OilliO Co., Ltd. and 10 g of Lipase QLM (Meito Sangyo Co., Ltd.) were fed into a 2000 ml reaction flask. After the enzymatic reaction carried out under stirring with a propeller at 50° C. for 17 hours, the reaction mixture was filtered to remove the remaining enzyme and thereby to obtain 980 g of the reaction mixture.

<The Second Reaction>

980 g of the reaction mixture obtained as described above, 3675 g of ethyl octanoate (trade name: Ethyl Octanoate, Inoue Perfumery Co., Ltd.), 1225 g of ethyl decanoate (trade name: n-Caprylic Acid Ethyl Ester, Tokyo Kasei Kogyo Co., Ltd.) and 120 g of Lipozyme TL (NOVO) were fed into 10 l reaction flask. After the enzymatic reaction carried out under stirring with a propeller at 40° C. for 26 hours, 5600 g of the reaction mixture was obtained. After the completion of the reaction, ethyl octanoate, ethyl decanoate, ethyl oleate and the medium chain fatty acid triglycerides were taken out of the reaction mixture to obtain 300 g of the triglyceride-containing mixture.

The respective components were taken out by the film distillation under the following conditions:
(1) Former step in the distillation: 25° C., 30 Pa; component (M) 4600 g
(2) Middle step in the distillation: 150° C., 1 Pa; component (N) 370 g
(3) Latter step in the distillation: 200° C., 1 Pa; component (O) 160 g.

The components (M) to (O) were analyzed by GLC to obtain the following results:
(M) Ethyl octanoate content: 75 mass % Ethyl decanoate content: 25 mass %
(N) Ethyl oleate content: 93 mass %
(O) Medium chain fatty acid triglyceride content: 70 mass %. (constituting fatty acids: 75 mass % of octanoic acid and 25 mass % of decanoic acid)

After the completion of the second reaction, the triglyceride-containing reaction mixture from which ethyl octanoate, ethyl decanoate, ethyl oleate and medium chain fatty acid triglycerides had been removed was analyzed by GLC and HPLC to find that the amount of the symmetric triglyceride comprising the medium chain fatty acids at the sn-1, 3 positions and oleic acid at the sn-2 position was 95 mass %. The fatty acids were composed of 50 mass % of octanoic acid, 17 mass % of decanoic acid and 33 mass % of oleic acid.

Example 6

Production of Symmetric Triglyceride Comprising Medium Chain Fatty Acids at sn-1,3 Positions and Unsaturated Fatty Acid having 18 Carbon Atoms at sn-2 Position:

<The First Reaction>

700 g of High Oleic castor oil (trade name: Olein Rich, Showa Sangyo Co., Ltd.), 300 g of medium chain fatty acid triglycerides (trade name: ODO, Nisshin OilliO Co. Ltd.) and 10 g of sodium methylate (trade name: Sodium Methoxide, Wako Pure Chemical Industries, Ltd.) were fed into a 2000 ml reaction flask. After the reaction carried out under stirring with a propeller at 50° C. for 2 hours, the reaction mixture was washed with water to remove remaining sodium methylate and also to obtain 970 g of the reaction mixture.

<The Second Reaction>

970 g of the reaction mixture obtained as described above, 3675 g of ethyl octanoate (trade name: Ethyl Octanoate, Inoue Perfumery Co., Ltd.), 1225 g of ethyl decanoate (trade name: n-Caprylic Acid Ethyl Ester, Tokyo Kasei K. K.) and 120 g of Lipozyme TL (NOVO) were fed into 10 liter reaction flask. After the enzymatic reaction carried out under stirring with a propeller at 40° C. for 26 hours, 5600 g of the reaction mixture was obtained. After the completion of the reaction, ethyl octanoate, ethyl decanoate, ethyl oleate and the medium chain fatty acid triglycerides were taken out of the reaction mixture to obtain 300 g of the triglyceride-containing mixture.

The respective components were taken out by the film distillation under the following conditions:
(1) Former step in the distillation: 25° C., 30 Pa; component (P) 4600 g
(2) Middle step in the distillation: 150° C., 1 Pa; component (Q) 370 g
(3) Latter step in the distillation: 200° C., 1 Pa; component (R) 160 g.

The components (P) to (R) were analyzed by GLC to obtain the following results:
(P) Ethyl octanoate content: 75 mass % Ethyl decanoate content: 25 mass %
(Q) Ethyl oleate content: 93 mass %
(R) Medium chain fatty acid triglyceride content: 70 mass %. (constituting fatty acids: 75 mass % of octanoic acid and 25 mass % of decanoic acid)

After the completion of the second reaction, the triglyceride-containing reaction mixture from which ethyl octanoate, ethyl decanoate, ethyl oleate and medium chain fatty acid triglycerides had been removed was analyzed by GLC and HPLC to find that the amount of the symmetric triglyceride comprising the medium chain fatty acids at the sn-1, 3 positions and oleic acid at the sn-2 position was 95 mass %. The fatty acids were composed of 50 mass % of octanoic acid, 17 mass % of decanoic acid and 33 mass % of oleic acid.

300 g of the symmetric triglyceride thus obtained was fed into a pressure reaction tank. 900 mg of a Ni catalyst was added thereto, and they were stirred under heating at 180° C. under hydrogen pressure of 0.3 MPa for 5 hours. After removing the catalyst, 300 g of the product was obtained. The product was analyzed by GLC and HPLC to find that the amount of the symmetric triglyceride comprising the medium chain fatty acids at the sn-1, 3 positions and stearic acid at the sn-2 position was 95 mass %. The fatty acids were composed of 50 mass % of octanoic acid, 17 mass % of decanoic acid and 33 mass % of stearic acid.

Example 7

The same procedure as that in Examples 5 and 6 were repeated except that 120 g of Lipozyme TL (NOVO) used in the second reaction was replaced with 12 g of a powdery enzyme obtained from *Rhizomucor miehei* to obtain the results similar to those in Examples 5 and 6.

As described above, MLM-type triglycerides having a high purity can be obtained by the process of the present invention for obtaining symmetric (MLM-type) triglycerides. MLM-type triglycerides of a high purity can efficiently be obtained on an industrial scale because wastes formed in the course of the production of the intended symmetric triglycerides, i. e. medium chain fatty acid triglycerides, alcohol monoesters of the medium chain fatty acids and alcohol monoesters of the long chain fatty acids, are effectively recycled as the starting materials.

What is claimed is:

1. A method for producing symmetric triglycerides, which comprises the steps of reacting a medium chain fatty acid triglyceride with a long chain fatty acid triglyceride in the presence of an enzyme or a chemical catalyst which is capable of catalyzing a random transesterification reaction to conduct a random transesterification reaction and thereby to obtain a reaction product containing a triglyceride composed of a medium chain fatty acid and a long chain fatty acid as the constituting fatty acids in the step of the first reaction; transesterifying the reaction product with an alcohol monoester of the medium chain fatty acid in the presence of an sn-1,3-position specific enzyme in the step of the second reaction and then taking the alcohol monoester of the medium chain fatty acid and the alcohol monoester of the long chain fatty acid out of the reaction product obtained by the second reaction to obtain the symmetric triglyceride composed of the medium chain fatty acids at the sn-1,3 positions and the long chain fatty acid at the sn-2 position.

2. The method of claim 1 wherein the medium chain fatty acid triglyceride is taken out after the completion of the first reaction.

3. The method of claim 2 wherein the medium chain fatty acid triglyceride, the alcohol monoester of the medium chain fatty acid and the alcohol monoester of the long chain fatty acid are taken out of the reaction product obtained by the second reaction, the medium chain fatty acid triglyceride taken out after the first and/or second reaction is recycled as the starting material for the first reaction, and the alcohol monoester of the medium chain fatty acid taken out after the second reaction is recycled as the starting material for the second reaction.

4. The method of claim 1 wherein the medium chain fatty acid triglyceride is taken out after the completion of the second reaction.

5. The method of claim 1 wherein the medium chain fatty acid triglyceride taken out after the second reaction is recycled as the starting material in the first reaction.

6. A method for producing symmetric triglycerides, which comprises the steps of reacting a medium chain fatty acid triglyceride with an alcohol monoester of a long chain fatty acid in the presence of an enzyme or a chemical catalyst which is capable of catalyzing a random transesterification reaction to conduct a random transesterification reaction and thereby to obtain a reaction product containing a triglyceride composed of a medium chain fatty acid and a long chain fatty acid as the constituting fatty acids in the first reaction; obtaining a triglyceride-containing product by removing the alcohol monoester of the medium chain fatty acid, the alcohol monoester of the long chain fatty acid and the medium chain-fatty acid triglyceride from the reaction product; transesterifying the triglyceride-containing product with the alcohol monoester of the medium chain fatty acid in the presence of an sn-1,3-position specific enzyme and then taking the alcohol monoester of the medium chain fatty acid and the alcohol monoester of the long chain fatty acid out of the reaction product obtained by the second reaction to obtain the symmetric triglyceride composed of the medium chain fatty acids at the sn-1, 3 positions and the long chain fatty acid at the sn-2 position.

7. The method of claim 6 wherein the medium chain fatty acid triglyceride is taken out after the completion of the second reaction.

8. The method of claim 6 wherein the medium chain fatty acid triglyceride taken out after the second reaction is recycled as the starting material in the first reaction.

9. The method of claim 6 wherein the alcohol monoester of the long chain fatty acid taken out after the second reaction is recycled as the starting material in the first reaction.

10. The method of claim 6 wherein the alcohol monoester of the medium chain fatty acid taken out after the second reaction is recycled as the starting material in the second reaction.

11. The method of claim 6 wherein the medium chain fatty acid triglyceride taken out after the first reaction is recycled as the starting material in the first reaction.

12. The method of claim 6 wherein the alcohol monoester of the long chain fatty acid taken out after the first reaction is recycled as the starting material in the first reaction.

13. The method of claim 6 wherein the alcohol monoester of the medium chain fatty acid taken out after the first reaction is recycled as the starting material in the second reaction.

14. The method of claim 6 wherein the alcohol monoester of the long chain fatty acid and medium chain fatty acid triglyceride taken out after the first reaction and/or second reaction are recycled as the starting materials in the first reaction, and the alcohol mono ester of the medium chain fatty acid taken out after the first reaction and/or the second reaction is recycled as the starting material in the second reaction.

15. A method for producing a symmetric triglyceride, which comprises the steps of reacting (a) a medium chain fatty acid triglyceride with (b) at least one member selected from the group consisting of a long chain fatty acid triglyceride, an alcohol monoester of a long chain fatty acid and a long chain fatty acid in the presence of an enzyme or a chemical catalyst which is capable of catalyzing a random transesterification reaction to conduct a random transesterification reaction and thereby to obtain the first reaction product containing a triglyceride composed of a medium chain fatty acid and a long chain fatty acid as the constituting fatty acids in the step of the first reaction; transesterifying the first triglyceride in the reaction product with (c) at least one member selected from the group consisting of alcohol monoester of the medium chain fatty acid and the medium chain fatty acid in the presence of an Sn-1,3-position specific enzyme to obtain the symmetric triglyceride composed of the medium chain fatty acid at the sn-1, 3 positions and the long chain fatty acid at the sn-2 position.

16. The method of claim 6 wherein the long chain fatty acid is a long chain unsaturated fatty acid.

17. The method of claim 16 wherein the long chain unsaturated fatty acid is one or more fatty acids selected from the group consisting of fatty acids having 18carbon atoms, EPA (eicosapentaenoic acid) and DHA (docosahexaenoic acid).

18. The method of claim 6 wherein the enzyme used for the first reaction and/or the second reaction is powdery lipase at least 90 mass % of which has a particle diameter of 1 to 100 μm and the enzymatic reaction is carried out in the absence of solvent and in anhydrous system.

19. The method of claim 18 wherein the first and/or second enzymatic reaction is carried out by sealing the powdery lipase and a filter aid into a filter and passing the starting materials through the filter.

20. The method of claim 1, wherein the enzyme comprises an unspecific lipase and the chemical catalyst comprises an alkaline catalyst or an acid catalyst.

21. The method of claim 6, wherein the enzyme comprises an unspecific lipase and the chemical catalyst comprises an alkaline catalyst or an acid catalyst.

22. The method of claim 15, wherein the enzyme comprises an unspecific lipase and the chemical catalyst comprises an alkaline catalyst or an acid catalyst.

* * * * *